United States Patent [19]

Fine

[11] Patent Number: 4,843,016

[45] Date of Patent: * Jun. 27, 1989

[54] DETECTION SYSTEM AND METHOD

[75] Inventor: David H. Fine, Framingham, Mass.

[73] Assignee: Thermedics Inc., Woburn, Mass.

[*] Notice: The portion of the term of this patent subsequent to Oct. 18, 2005 has been disclaimed.

[21] Appl. No.: 19,029

[22] Filed: Feb. 26, 1987

Related U.S. Application Data

[63] Continuation of Ser. No. 512,374, Oct. 7, 1974, Pat. No. 4,778,764.

[51] Int. Cl.⁴ .................................. G01N 21/76
[52] U.S. Cl. .................................. 436/106; 436/116; 436/161; 436/172; 422/52; 422/70; 422/80
[58] Field of Search ............... 436/106–118, 436/161, 155, 159, 160, 172; 422/70, 52, 28, 80

[56] References Cited

U.S. PATENT DOCUMENTS

| | | | |
|---|---|---|---|
| 3,207,585 | 9/1965 | Glass et al. | 436/158 |
| 3,518,059 | 6/1970 | Levy | 436/158 |
| 3,647,387 | 3/1972 | Benson et al. | 436/107 |
| 3,650,696 | 3/1972 | Eads | 436/96 |
| 3,746,513 | 7/1973 | Warnick et al. | 436/116 |
| 3,877,875 | 4/1975 | Jones | 436/114 |

OTHER PUBLICATIONS

Hadden et al., Basic Liquid Chromatography.
Pankov et al., Ind. Lab., vol. 40, No. 2, pp. 194–195, Aug. 1974.
Fontijn et al., Anal Chem., vol. 42, No. 6, May 1970.
Heusden, Philips Tech. Rev. 34, 73–81, 1974, No. 2/3.

Primary Examiner—Michael S. Marcus
Attorney, Agent, or Firm—Darby & Darby

[57] ABSTRACT

A detection system for detecting the presence of predetermined compounds in a sample. The system comprises a sample injection means, a chromatographic column, a conversion means and one or more specific gas detectors. The conversion means transforms the column effluent to combustion products in the gas phase, after which those combustion products are transferred to the specific gas detectors. In one embodiment for detecting nitrogen compounds, the conversion means includes an oxygen-rich flame, a means to control the flame to have a temperature in the range 600°–1700° C., means to inject the column effluent into the flame, and an input port for transferring the flame effluent to a specific nitrogen detector.

36 Claims, 2 Drawing Sheets

DETECTION SYSTEM AND METHOD

This is a continuation, of application Ser. No. 512,374, filed Oct. 7, 1974, now U.S. Pat. No. 4,778,764.

BACKGROUND OF THE INVENTION

This invention relates to a method and apparatus for detecting the presence of predetermined compounds in a sample, particularly to liquid and gas chromatographic detection techniques for application to chromatographic analysis of samples containing nitrogen, sulphur, carbon and halogen compounds.

Systems utilizing chromatographic techniques for separation of components in samples are well known in the art. All such systems rely on differential migration processes where the components of a sample in a moving phase are selectively retained by a stationary phase. The moving phase may be a gas, as in gas chromatographic systems, or a liquid, as in liquid chromatographic systems. The stationary phase in either of such systems may be either liquid or a solid.

The early Nobel prize winning work of A. J. P. Martin and R. L. M. Synge (Biochem. J. 35, 91, 1358 (1941) set forth the basic liquid chromatographic techniques used in systems today. However, practical applications for these techniques have been severely limited by detector development. As a result, liquid chromatographic analysis has been generally a lengthy procedure, often taking hours and even days.

Recently, detectors characterized by relatively high sensitivity, low noise, and wide linear response range, have become increasingly available. Such detectors include UV absorption, refractive index, micro-adsorption and flame ionization detectors, and the more limited range electrical conductivity and fluorescence detectors. Furthermore, high pressure fluid pumps (in excess of 5000 psi) have also become available, permitting the use of long, narrow bore (e.g. 1 mm) columns having small diameter packing particles. This combined development of high pressure pumps and high performance detectors for use with high performance narrow bore columns, has reduced the time required for liquid chromatographic analysis from hours to minutes in many cases. However, even using such elements, the known liquid chromatographic detection systems only provide analysis of liquid samples with sensitivity as high as one part in $10^6$ in particularly favorable cases, such as where the compound has a strong UV absorption band for UV detection at the corresponding wavelength.

Gas chromatographic detection systems have been developed primarily since the paper by A. J. P. Martin and A. T. James (Analyst 77, 915 (1952)). One disadvantage of such systems, as compared to liquid detection systems, is the occurance of breakdown of a liquid sample at the vaporization temperatures applied at the input to the column and at the high temperatures applied at the column itself (these latter temperatures being maintained to decrease the retention time of the column). In spite of this disadvantage, gas chromatographic systems have received far more attention than the liquid detection systems because of the availability of higher sensitivity and faster response detectors. Specifically, known gas detectors include the flame ionization detector (FID) which is highly sensitive to any compound containing carbon, the electron capture detector (EC) which is highly sensitive to halogen compounds, and the thermal conductivity detector (TC) which is highly sensitive to all compounds (a general or "universal" detector). However, these detectors also have significant sensitivities to other compounds which may mask responses from desired compounds, thereby rendering such detectors unsuitable for use in the detection of those desired compounds. For example, in the case of halogen detection using an electron capture detector, both the alcohol and halogen compound content of the sample produce interfering responses. For the specific detection of nitrogen compounds, two commercial detectors are available: the Coulson detector and an adaptation of the FID. Both have nitrogen sensitivities substantially less than one part in $10^9$ and both are extraordinarily difficult to operate.

SUMMARY OF THE INVENTION

An object of the present invention is to provide a method and system for the high speed analysis of a sample in a liquid phase solvent.

It is another object to provide a system for high sensitivity chromatographic analysis of a sample in a liquid phase solvent.

Still another object is to provide a high sensitivity analysis system for detecting the presence of nitrogen, sulphur, halogen and/or carbon compounds in a sample in a liquid phase solvent or a carrier gas.

Fundamentally, the invention involves an oxidizing conversion means, means for presenting a sample to the conversion means and detector means for processing effluent from the conversion means.

For a sample in a liquid phase solvent, a preferred detection system in accordance with the present invention may include a high pressure liquid chromatograph having a solvent reservoir, a high pressure pump, a sample injector and a column having an output port. The system further includes a conversion means connected to the column output port for transforming the column effluent to combustion products in the gas phase. The system additionally includes one or mroe specific gas detectors, each having an input port connected to the conversion means for receiving the column effluent. In one embodiment capable of detecting sulphur, carbon, halogen and/or nitrogen compounds, the conversion means comprises an oxygen-rich flame and an injection means for injecting the column effluent into the flame. The specific gas detectors may take the form of a sulphur dioxide ($SO_2$) detector, a carbon dioxide ($CO_2$) detector and/or an electron capture detector for halogen compounds. In the detection of nitrogen compounds, this embodiment preferably includes means to control the flame to have a temperature in the range 600°–1700° C., together with a nitric oxide (NO) detector. One version of the nitric oxide detector includes a means for reacting the flame effluent with ozone ($O_3$) and a means for detecting light from the resultant chemiluminescent reaction (i.e. light having wavelength in the range 0.6–2.8 microns). Other nitric oxide detectors, such as electro chemical sensors, may be used.

In operation, upon injection into the oxygen-rich flame, the nitrogen compounds of the column effluent are converted to nitric oxide and non-nitrogen compounds, the sulphur compounds to sulphur dioxide and non-sulphur compounds, the carbon compounds to carbon dioxide and non-carbon compounds. In the temperature range of the flame, these conversions are substantially complete.

These resultant compounds are then applied to the specific detectors connected to the burner and the various specific gasses are detected with the characteristic sensitivity of such detectors, i.e. in the range one part in $10^6$ to $10^9$. It will be understood that an appropriate solvent may be selected to dissolve the sample so that none of the elements-to-be-detected are present therein. As a result, trace compounds may be detected without being masked by the solvent, or without requiring removal of the solvent prior to detection.

Thus, the combination of a liquid chromatographic column with the conversion means of the present invention and the specific gas detectors, provides a system wherein the advantages of liquid over gas chromatography may be attained while retaining the high sensitivity associated with the specific gas detectors, i.e. one part in $10^6$ to $10^9$.

For samples mixed with a gas phase carrier, the present invention may utilize a gas chromatographic column in conjunction with an injection port and a conversion means and one or more specific gas detectors. The conversion means in such systems is substantially similar to that described above for the liquid chromatographic detection systems and performs a similar function thereto.

An advantage of the present invention is attained wherein the flame is effective to transform the sample to combustion products which are not detected by the specific gas detectors. For example, the alcohol content of a sample is converted by the flame to water and carbon dioxide, neither of which affect the response of an electron capture detector, thereby permitting use of such a detector in the halogen compound detection of samples which may contain trace amount of alcohol. Another specific advantage attained using this conversion means is that the atmospheric nitrogen in the carrier gas is not converted to an oxide of nitrogen in the temperature range of the burner flame and thus, the background noise for nitrogen detection is maintained at a substantially low level. This is particularly important using the nitric oxide detector described above wherein the flame effluents are reacted with ozone and the light emitted by the resultant chemiluminescent reaction is detected to obtain detection sensitivity at least one part in $10^9$.

In alternative forms, the invention may be embodied with an oxygen-rich furnace having an input port for receiving the sample. Similar to the above described embodiment, the sample may be effluent from either liquid or gas column effluent (and, for nitrogen compound detection systems, with the furnace being maintained in the temperature range 600°–1700° C.).

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
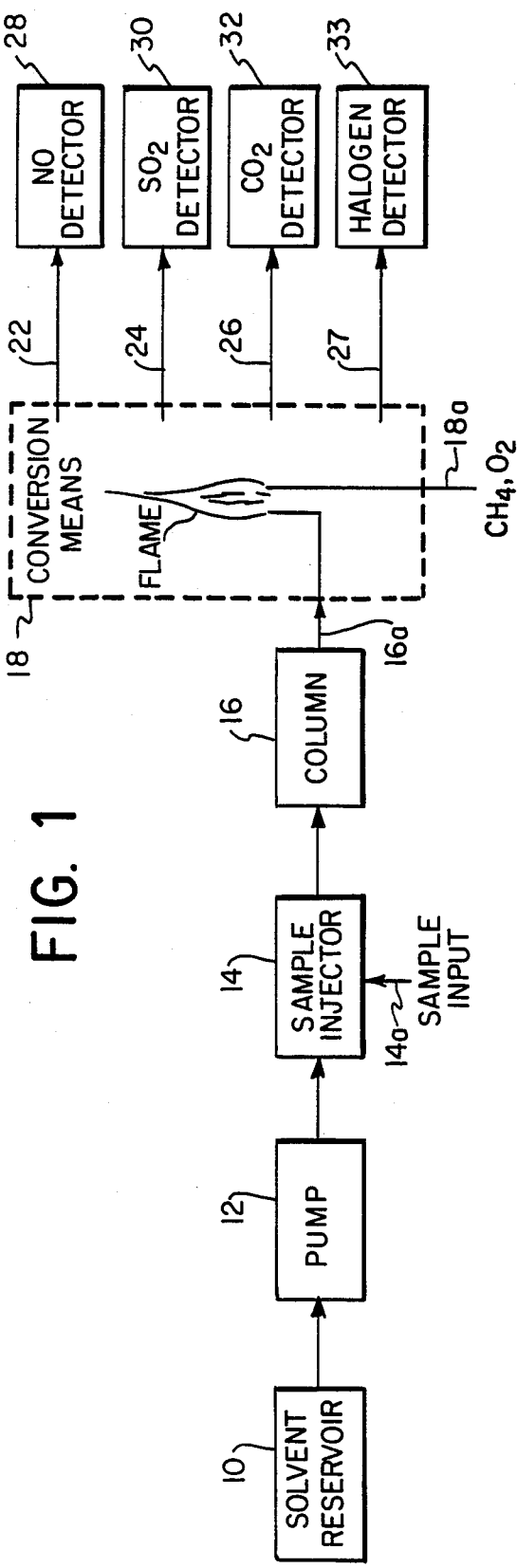
FIGS. 1 and 3 show in block diagram form detection systems for analyzing samples in a liquid phase carrier.
Figure 2:
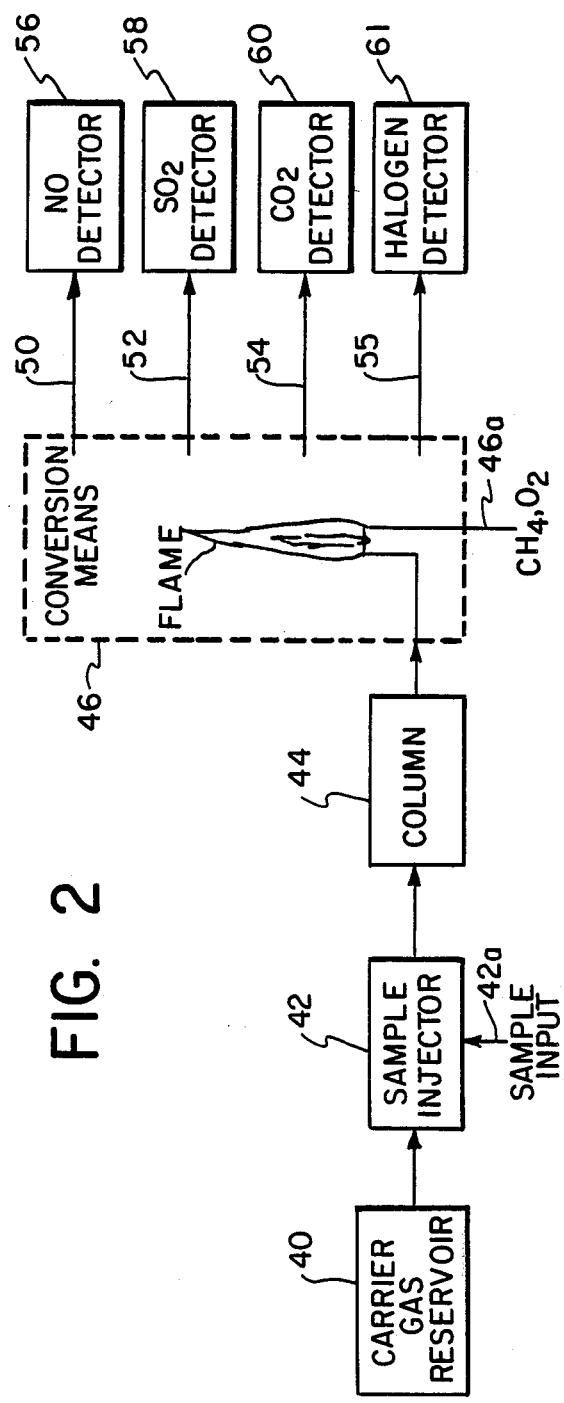
FIGS. 2 and 4 show in block diagram form detection systems for analyzing samples in a gas phase carrier.

FIGS. 1 and 2 will be described in connection with chromatographic means for presenting the sample to the conversion means.

FIG. 1 illustrates an LG chromatographic (Liquid chromatograph/Gas detector) detection system in accordance with the present invention for use with liquid samples. That system includes a solvent reservoir 10 connected to a high pressure pump 12 such as the model 600 manufactured by Waters Associates, Milford, Massachusetts. The high pressure pump 12 may provide an output pressure as high as 6000 psi in the fluid coupling to the injector 14. The injector 14 includes an input port 14a for receiving a sample in liquid phase. The output of injector 14 is connected to liquid chromatograph column 16. The column may be a high performance column such as a 1 meter, 2 mm inner diameter stainless steel tube which is maintained at a temperature in the range 0° to 100° C.

The column output port 16a is connected to the conversion means 18. Conversion means 18 includes in the present embodiment, a flame (preferably oxygen-rich) fueled by a methane-air (or oxygen) mixture supplied via input port 18a. The column effluent is injected into that flame via a central aperture.

It will be understood that the fuel in the present embodiment is methane, but alternative hydrocarbon or other fuels may be used in other embodiments. In addition, other embodiments in keeping with the present embodiment may utilize a flame which is not oxygen-rich, although such embodiments are somewhat less efficient than the present one.

In order to achieve a flame temperature in the range of 600°–1700° C. for detecting nitrogen compounds using the present embodiment, the ratio of air-to-methane is controlled to be at least 120% of stoichiometric (i.e. at least 20% excess air). When oxygen is used instead of air, at least 500% of the stoichiometric amount of oxygen is required. Alternatively, the flame temperature may be controlled by placing heat radiators close to the flame front.

The conversion means 18 further includes a regulator and pumps to maintain the pressure therein to be in the range 5 torr to 5 atmospheres. The output ports 22, 24, 26 and 27 of conversion means 18 are shown to be connected to specific gas detectors 28, 30, 32 and 33, respectively. As indicated, detectors 28, 30, 32 and 33 detect nitric oxide (NO), sulphur dioxide ($SO_2$), carbon dioxide ($CO_2$), and halogen compounds, respectively. It will be understood that in other embodiments only selected ones of these detectors may be used, depending on the compounds to be detected.

For the detection of nitrogen compounds in the sample, the nitric oxide detector 28 comprises a means for reacting the flame effluent with ozone ($O_3$). This reaction takes the form:

$$NO + O_3 \rightarrow NO_2^* + O_2$$

$$NO_2^* \rightarrow NO_2 + h\lambda$$

where the wavelength $\lambda$ of the light produced is in the range 0.6–2.8 microns and where $NO_2^*$ denotes an electronically excited form of nitrogen dioxide. The above chemiluminescent reaction is described more fully in Clough, P.N. and Thrush, B.A., "Mechanism of Chemiluminescent Reaction between Nitric Oxide and Ozone," Trans. Faraday Soc. 63, 915 (1967). The NO detector 28 further includes a means for detecting the light produced by the above-noted chemiluminescent reaction. As described, the nitric oxide detector 28 is of the same form described in U.S. Pat. No. 3,763,877, issued Oct. 9, 1973 in the name of David T. Lieb, assigned to the assignee of this application and entitled "Fluid Flow Control System," incorporating a chemiluminescent reaction chamber, and associated photosensitive device.

In the present embodiment, the flow rate of the sample passing through the column is preferably in the range 1-10 cm$^3$ per minute with a pressure near the column input port in the range 100-12,000 psi. In order to effectively inject the column effluent into the flame, an atomizing nozzle may be used, or the liquid may be directly burned if it is flammable by injecting the liquid into the flame. Alternatively, the liquid may be burned on a candle wick.

Using any of these flame injection techniques, the sample solvent is vaporized or converted to non-interfering combustion compounds while simultaneously any nitrogen in the sample is converted into nitric oxide. Similarly, any sulphur in the column effluent is converted into sulphur dioxide and carbon compounds into carbon dioxide. It will be understood that the solvent for the sample is selected to be free from nitrogen, sulphur, carbon and/or halogens, depending on which elements are to be detected, so that the solvent does not contribute to the nitric oxide, sulphur dioxide, carbon dioxide and/or halogen compound content of the flame-effluent. Thus, the conversion means converts the column effluent containing nitrogen, sulphur, carbon and-/or halogen compounds by passing it through the flame under the controlled temperature and pressure conditions. The flame effluent is in the gas phase with its nitrogen content in the form of nitric oxide, sulphur content in the form of sulphur dioxide, and carbon content in the form of carbon dioxide. It will be understood that, with appropriate solvent selection, each of the specific gas detectors is not affected by the solvent combustion products and senses only the corresponding oxides or halogen compound associated therewith.

In alternative embodiments, the conversion means 18 may comprise a furnace, preferably oxygen-rich and maintained at a pressure in the range 5 torr to 5 atmospheres and at a moderately high to high temperature, e.g. in the range 600°-3000° C. Temperatures somewhat below 600° may be utilized, depending upon the sample content and use of appropriate catalysts to foster the desired sample reaction. For the detection of nitrogen compounds, the furnace is maintained at a moderately high temperature, e.g. in the range 600°-1700° C., although lower temperatures may be used with appropriate catalysts.

Figure 3:
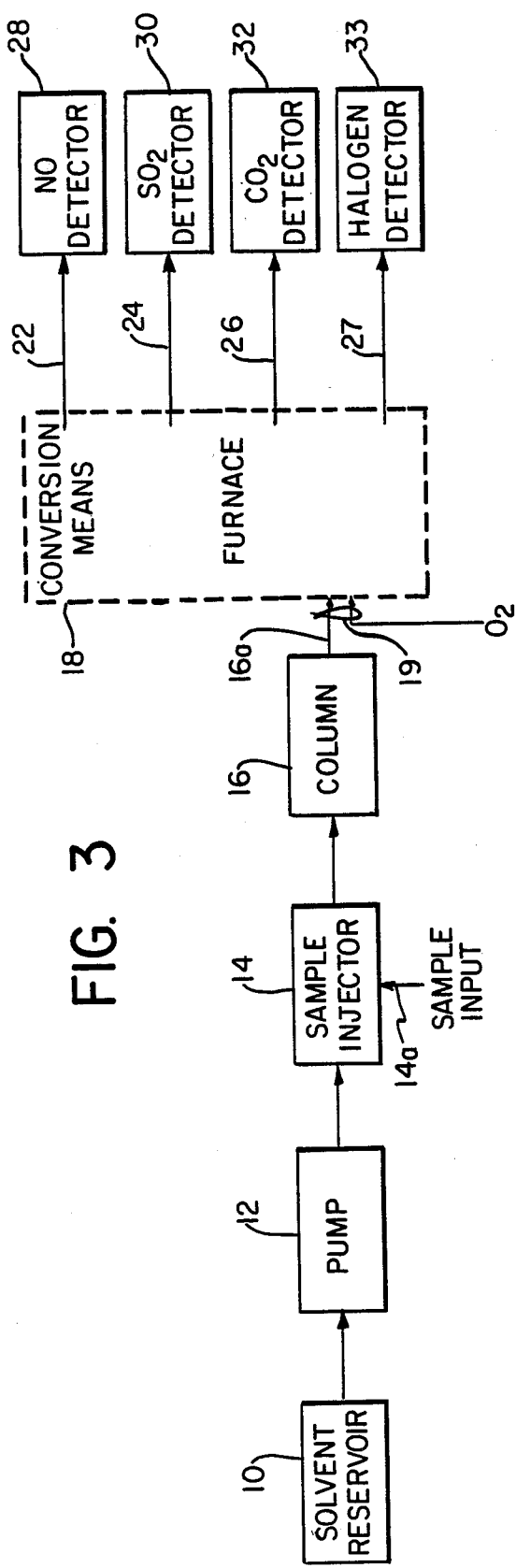

An LC-furnace embodiment is illustrated in FIG. 3 wherein elements corresponding to those illustrated in FIG. 1 are identified with the same reference designations.

In the furnace embodiment, the column effluent is transferred, together with oxygen, directly into an input port 16a in the furnace. For highest efficiency, the furnace may be maintained with an oxygen-rich environment, i.e. more than the stoichiometric quantity of oxygen for reaction with the sample and solvent. However, in other embodiments, a lesser proportion of oxygen may be present in the furnace resulting in reduced efficiency.

It will be understood that the conversion means embodiment including an oxygen-rich flame is somewhat more efficient than the furnace embodiment due to the exposure in the flame of the intermediate free radical and ionic species which aid in the conversion of the column effluent to the combustion products. Furthermore, the transit time of the combustion products across the furnace must be accommodated in the resultant calculations based on the detector outputs.

FIG. 2 shows a GG chromatographic (Gas chromatograph/Gas detector system) detection system for use with a sample which may contain nitrogen, sulphur, carbon and/or halogen compounds in a carrier gas. For that system, a carrier gas reservoir 40 provides a flow of carrier gas via sample injector 42 through the chromatograph column 44. A sample is introduced in either liquid or gas phase to injector 42 via sample port 42a. The output port of the column 44 is connected to the conversion means 46 which has, in addition, a fuel input port 46a and output ports 50, 52, 54 and 55. It will be understood that the carrier gas is selected to be free from nitrogen, sulphur, carbon and/or halogens, depending on which elements are to be detected.

The output ports 50, 52, 54 and 55 are connected to specific gas detectors 56, 58, 60 and 61 for detecting nitric oxide, sulphur dioxide, carbon dioxide and halogen compounds, respectively. In other embodiments, fewer detectors may be used, depending on which compounds are to be detected. The conversion means includes a pressure regulator to maintain the pressure therein in the range 5 torr-5 atmospheres.

For the present embodiment, the conversion means includes a burner having an oxygen-rich flame fueled by a methane-oxygen mixture. Although the oxygen-rich characteristic of the flame of the present embodiment provides for highest efficiency operation, less than stoichiometric amounts of oxygen may also be utilized in keeping with the present invention. As with the embodiment described above, alternative hydrocarbon or other fuels may be used in different embodiments. Further, the present embodiment also includes a means to control the flame temperature to be in the range 600°-1700° C. to permit detection of nitrogen compounds.

Figure 4:
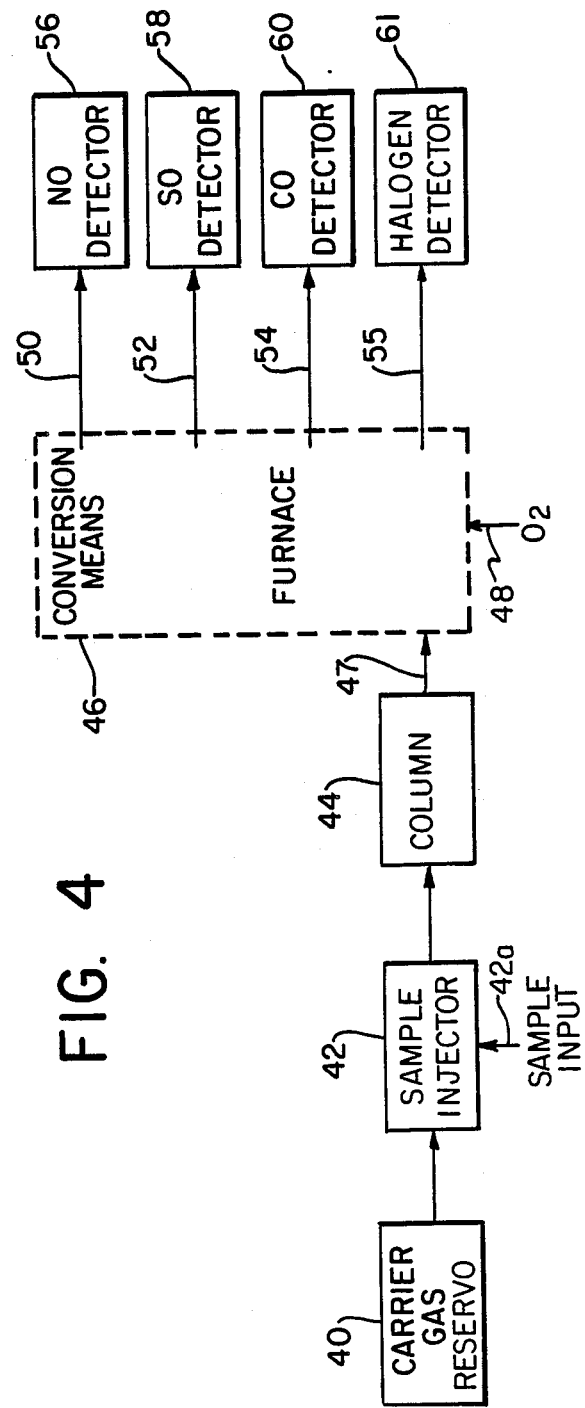

An alternative GC embodiment is illustrated in FIG. 4 wherein elements corresponding to those illustrated in FIG. 2 are identified with the same reference designations, and wherein the conversion means 18 comprises a furnace having an input port 47 for receiving the column effluent with a second input port 48 for receiving oxygen (O$_2$). In this latter embodiment, the furnace is maintained with the pressure therein in the range 5 torr-5 atmospheres and a moderately high to high temperature, e.g. in the range 600°-3000° C. Temperatures somewhat below 600° C. may be utilized depending on the sample content and the use of appropriate catalysts to foster the desired sample reaction.

For the detection of nitrogen compounds, the furnace is further maintained at a moderately high temperature, e.g. in the range 600°-1700° C. (although lower temperatures may be used with appropriate catalysts) so that nitrogen in the carrier gas or from atmospheric leakage does not contribute to the NO content of the furnace effluent.

In operation, the gas chromatograph/gas detector (GG)-embodiment is substantially similar to the above-described liquid chromatograph/gas detector (LG) embodiment. The injector 42 injects portions of the sample into the flow of carrier gas from the reservoir 40 to the column 44. The column effluent is similarly converted in conversion means 46 into the following combustion products: the nitrogen in the sample is converted to nitric oxide, the sulphur to sulphur dioxide, and the carbon to carbon dioxide. These reactions are substantially complete under the temperature and pressure conditions present in the conversion means. The resultant effluent from the conversion means is similarly applied to nitric oxide, sulphur dioxide, carbon dioxide and/or halogen detectors, depending on the compounds to be detected.

The invention may, of course, be embodied in other forms without departing from the essential characteristics thereof. The present embodiment is therefore to be considered in all respects as illustrative and not restrictive, the scope of the invention being indicated by the appended claims rather than by the foregoing description.

I claim:

1. The method of determining the quantity of a nitrogen compound in a sample of material containing nitrogen, without interference from atmospheric nitrogen comprising the steps of:
   a. combining said sample with a carrier gas,
   b. passing said combination through a gas chromatograph,
   c. heating the effluent from said chromatograph in an oxygen-rich atmosphere at a temperature less than about 600° C. in the presence of a catalyst to convert said compound to nitric oxide (NO) in a single step, while not converting atmospheric nitrogen,
   d. causing the nitric oxide produced by such heating to undergo a chemiluminescent reaction with ozone, and
   e. determining the magnitude of the chemiluminescent reaction to indicate the quantity of said nitrogen compound in said sample, whereby said indication is made independent of contaminating nitrogen in said carrier or from atmospheric leakage.

2. The method of determining the quantity of a nitrogen compound in a sample comprising the steps of
   a. combining said sample with a carrier gas;
   b. passing said combination through a gas chromatograph;
   c. heating the effluent from said chromatograph in an oxygen-rich atmosphere at a temperature of at least 600° C. to convert nitrogen compounds to nitric oxide (NO) in a single step,
   d. causing said nitric oxide to undergo a chemiluminescent reaction with ozone to produce light energy, and
   e. indicating the magnitude of said light energy in the wavelength range from about 0.6 to 2.8 microns, whereby the quantity of said compound in a constituent of said effluent may be determined by said indication.

3. The method of determining the total nitrogen content of a sample of material containing organically bound nitrogen comprising the steps of:
   a. injecting said sample into an oxygen-rich flame to convert said sample into gaseous combustion products, said flame being at a temperature sufficiently above 600° C. so that substantially all of the bound nitrogen is converted to nitric oxide (NO) in a single step,
   b. reacting the nitric oxide produced by such combustion with ozone to produce chemiluminescence, and
   c. determining the magnitude of said chemiluminescence to indicate the quantity of bound nitrogen in said sample.

4. The method of claim 3 wherein said sample is a gas effluent from a gas chromatograph.

5. The method of claim 3 wherein said sample is a liquid effluent from a liquid chromatograph.

6. The method of claim 2 wherein said temperature is within the range of about 600° C.–1700° C.

7. The method of claim 3 wherein said temperature is within the range of about 600° C.–1700° C.

8. The method of claim 4 wherein said temperature is within the range of about 600° C.–1700° C.

9. The method of claim 3 wherein the amount of oxygen is at least 120% of stoichiometric.

10. The method of determining the total nitrogen content of a sample of nitrogen-containing material comprising the sequential steps of:
    a. dissolving said sample in a liquid solvent forming a solution, said solvent having in it none of the nitrogen desired to be determined;
    b. pumping said solution into a high-pressure liquid chromatograph having a long, narrow-bore column at a pressure in the range of 100 to 12,000 psi, with a flow rate of 1–10 cc/min., to separate the sample into various constituents and thereby producing a liquid-phase chromatograph effluent having said constituents distributed in time;
    c. converting said chromatograph effluent into gaseous combustion products by (i) establishing a flame with a hydrocarbon fuel, (ii) injecting said chromatograph effluent into said flame, (iii) supplying oxygen to said flame where the amount of oxygen is at least 120% of stoichiometric, (iv) maintaining a flame temperature in the range 600 to 1700° C., thereby converting substantially all of said nitrogen content to nitric oxide (NO) in a single step;
    d. transferring said combustion products to a gas detector for nitric oxide (NO);
    e. causing said combustion products to react within said nitric oxide detector chemiluminescently with ozone ($O_3$) to form oxygen ($O_2$), nitrogen dioxide ($NO_2$) and light energy;
    f. detecting the intensity of said light energy having wavelength in the range of 0.6–2.8 microns to determine the magnitude of the chemiluminescent reaction, whereby the presence of at least one part in $10^9$ of nitrogen in said sample may be determined to at least one part in $10^9$.

11. The method of determining the total nitrogen content of a sample of nitrogen-containing material comprising the sequential steps of:
    a. combining said sample with a carrier gas;
    b. passing the combined sample and carrier gas through a gas chromatograph for separation into various constituents and thereby producing a gas-phase chromatograph effluent;
    c. converting said chromatograph effluent into gaseous combustion products by (i) establishing a flame with a hydrocarbon fuel, (ii) injecting said chromatograph effluent into said flame, (iii) supplying oxygen to said flame, wherein the amount of oxygen is at least 120% stoichiometric, (iv) maintaining a pressure at said flame in the range of 5 torr to 5 atmospheres, and (v) maintaining a flame temperature in the range of about 600° C. to 1700° C., thereby converting substantially all of said nitrogen content to nitric oxide (NO) in a single step;
d. transferring said combustion products to a nitric oxide (NO) gas detector;
e. causing said combustion products to react within said nitric oxide detector chemiluminescently with ozone ($O_3$) to form oxygen ($O_2$), nitrogen dioxide ($NO_2$) and light energy;
f. and detecting the intensity of said light energy having wavelength in the range of 0.6-2.8 microns to determine the magnitude of the chemiluminescent reaction, whereby the presence of at least one part in $10^9$ of nitrogen in said sampler may be determined to at least one part in $10^9$.

12. The method of determining the total nitrogen content of a sample of nitrogen-containing material comprising the sequential steps of:
a. dissolving said sample in a liquid solvent forming a solution, where said solvent has present in it none of the nitrogen desired to be determined;
b. pumping said solution into a high-pressure liquid chromatograph having a long, narrow-bore column at a pressure in the range of 100-12,000 psi, with a flow rate of 1-10 cc/min. to separate the sample into various constituents and thereby producing a liquid-phase chromatograph effluent having said constituents distributed in time.
c. converting said chromatograph effluent into gaseous oxidation products by heating said effluent in a furnace, in the presence of oxygen ($O_2$) in greater than stoichiometric quantity, at a pressure in the range of 5 torr to 5 atmospheres and at a furnace temperature below 1700° C., thereby converting substantially all of said nitrogen content to nitric oxide (NO) in a single step;
d. transferring said combustion products to a nitric oxide gas detector (NO);
e. causing said oxidation products to react within said nitric oxide detector chemiluminescently with ozone ($O_3$) to form oxygen ($O_2$), nitrogen dioxide ($NO_2$) and light energy;
f. detecting the intensity of said light energy having wavelength in the range of 0.6-2.8 microns to determine the magnitude of the chemiluminescent reaction, whereby the presence of at least one part in $10^9$ of nitrogen in said sample may be determined to at least one part in $10^9$.

13. The method of determining the total nitrogen content of a sample of nitrogen-containing material comprising the sequential steps of:
a. combining said sample with a carrier gas;
b. passing the sample and carrier gas through a gas chromatograph for separation into various constituents and thereby producing a gas-phase chromatograph effluent;
c. converting said chromatograph effluent into gaseous oxidation products by heating said effluent in a furnace in the presence of oxygen ($O_2$), at a pressure in the range of 5 torr to 5 atmospheres and at a furnace temperature below 1700° C., thereby converting substantially all of said nitrogen content to nitric oxide (NO) in a single step;
d. transferring said oxidation products to a nitric oxide detector;
e. causing said oxidation products to react within said nitric oxide detector chemiluminescently with ozone ($O_3$) to form oxygen ($O_2$), nitrogen dioxide ($NO_2$) and light energy;
f. detecting the intensity of said light energy having wavelength in the range of 0.6-2.8 microns to determine the magnitude of the chemiluminescent reaction, whereby the presence of at least one part in $10^9$ of nitrogen in said sample may be determined to at least one part in $10^9$.

14. Apparatus for determining the quantity of a nitrogen compound in a sample of material containing nitrogen, without interference from atmospheric nitrogen, comprising:
(a) a chromatograph to be supplied with said sample,
(b) a converter coupled to said chromatograph for heating the effluent from said chromatograph in an oxygen-rich atmosphere at a temperature less than about 600° C. in the presence of a catalyst to convert said compound to nitric oxide (NO) while not converting atmospheric nitrogen,
(c) means causing the nitric oxide produced by such heating to undergo a chemiluminescent reaction with ozone, and
(d) means determining the magnitude of the chemiluminescent reaction to indicate the quantity of said nitrogen compound in said sample.

15. Apparatus for determining the quantity of a nitrogen compound in a sample combined with a carrier, comprising
(a) a chromatograph to be supplied with said sample and carrier;
(b) a converter for heating the effluent from said chromatograph in an oxygen-rich atmosphere at a temperature of at least 600° C. to convert nitrogen compounds to nitric oxide (NO),
(c) means causing said nitric oxide to undergo a chemiluminescent reaction with ozone to produce light energy, and
(d) means indicating the magnitude of said light energy in the wavelength range from about 0.6 to 2.8 microns, whereby the quantity of said compound in a constituent of said effluent may be determined by said indication.

16. The apparatus of claim 15 wherein said temperature is within the range of about 600° C.-1700° C.

17. Apparatus for determining the nitrogen content of a sample of material containing organically bound nitrogen, comprising:
(a) a chromatograph for receiving said sample,
(b) means for converting the output of said chromatograph into gaseous conversion products, at a temperature sufficiently above about 600° C. so that substantially all of the bound nitrogen is converted to nitric oxide (NO),
(c) means reacting the nitric oxide produced by such conversion with ozone to produce chemiluminescence, and
(d) means determining the magnitude of said chemiluminescence to indicate the quantity of bound nitrogen in said sample.

18. The apparatus of claim 17 wherein said temperature is within the range of about 600° C.-1700° C.

19. Apparatus for determining the nitrogen content of a sample of nitrogen-containing material dissolved in a liquid solvent to form a solution, where said solvent has present in it none of the nitrogen desired to be determined, said apparatus comprising;
(a) a liquid chromatograph having a long, narrow-bore column, (b) means for passing said solution through said chromatograph at a pressure in the range of about 100-12,000 psi and with a flow rate of about 1-10 cc/min. to separate the sample into various constituents and thereby produce a liquid-phase chromatograph effluent having said constituents distributed in time;

(c) means adapted in the presence of oxygen ($O_2$) at a pressure in the range of about 5 torr to 5 atmospheres and at a temperature below 1700° C., to convert substantially all of said nitrogen content to nitric oxide (NO);

(d) a nitric oxide gas detector (NO) adapted to cause said nitric oxide to react within said detector chemiluminescently with ozone ($O_3$) to form oxygen ($O_2$), nitrogen dioxide ($NO_2$) and light energy; and (e) a detector for the intensity of said light energy having wavelength in the range of about 0.6-2.8 microns to determine the magnitude of the chemiluminescent reaction, whereby the quantity of nitrogen in said sample may be determined.

20. Apparatus for determining the nitrogen content of a sample of nitrogen-containing material combined with a carrier gas comprising:

(a) a gas chromatograph adapted to separate said sample and carrier gas into various constituents and thereby produce a gas-phase chromatograph effluent;

(b) a pyrolyzer for converting said chromatograph effluent into gaseous products in the presence of oxygen ($O_2$), at a temperature below about 1700° C., thereby converting substantially all of said nitrogen content to nitric oxide (NO);

(c) a nitric oxide detector adapted to cause said oxidation products to react within said detector chemiluminescently with ozone ($O_3$) to produce light energy, and (d) means for detecting the intensity of said light energy to determine the magnitude of the chemiluminescent reaction, whereby the quantity of nitrogen in said sample may be determined.

21. Apparatus for determining the presence of a nitrogen compound in a sample of material containing nitrogen, without interference from atmospheric nitrogen, comprising:

(a) a source of carrier gas, (b) means for combining said sample with said carrier gas to produce a combination of carrier gas and sample, (c) a gas chromatograph responsive to said combination to provide an effluent from said chromatograph, (d) a pyrolyzer for heating said effluent with added oxygen to a temperature less than about 600° C. in the presence of a catalyst to convert said compound to nitric oxide while not converting atmospheric nitrogen, and (e) a detector responsive to said effluent to indicate the presence of nitric oxide, to thereby indicate the presence of said nitrogen compound in said sample, independent of contaminating nitrogen in said carrier or from atmospheric leakage.

22. Apparatus for determining the presence of a nitrogen compound in a sample comprising:

(a) a chromatograph responsive to said sample to provide an effluent exiting from said chromatograph;

(b) means for heating the effluent from said chromatograph at a temperature of at least 600° C. to convert nitrogen compounds to nitric oxide; and (c) a detector to indicate the presence of nitric oxide in said heated effluent, whereby the presence of said nitrogen compound in a constituent of said effluent may be determined by said indication.

23. The apparatus of claim 22 wherein said chromatograph is a gas chromatograph.

24. The apparatus of claim 22 wherein (a) said chromatograph includes means for providing effluent components exiting said chromatograph at differing times and corresponding respectively to constituents of said sample, and wherein (b) said detector includes means for indicating the presence of individual effluent components.

25. The method of determining the presence of a nitrogen compound in a sample, comprising the steps of:

(a) producing an effluent having components of said sample separated in time, (b) heating said effluent at a temperature of at least 600° C. to convert nitrogen compounds to nitric oxide; and (c) indicating the nitric oxide level for said effluent components, whereby the presence of said compound may be determined.

26. The method as in claim 25 of determining the presence of a nitrogen compound in a sample of material containing nitrogen, comprising the step of indicating the nitric oxide level produced by each of said effluent components;

whereby the presence of said compound may be determined.

27. The method of determining the presence of a nitrogen compound in a sample of material containing organically bound nitrogen comprising the steps of:

(a) chromatographically separating constituents of the sample;

(b) heating said separated constituents to convert bound nitrogen to nitric oxide, and (c) determining the magnitude of the nitric oxide thereby produced from said constituents to indicate the presence of nitrogen in said sample.

28. The method of claim 27 comprising the steps of causing the nitric oxide produced by such heating to undergo a chemiluminescent reaction, and indicating the magnitude of said reaction.

29. The method of claim 27 wherein said heating is performed at a temperature in excess of 600° C.

30. The method of claim 29 wherein said heating is performed at a temperature within the range of about 600° C. to 1700° C.

31. The method of determining the presence of a nitrogen compound in a sample of material containing organically bound nitrogen comprising the steps of (a) passing said sample through a chromatograph to provide an effluent;

(b) injecting said effluent into a pyrolyzer together with oxygen to convert said sample into gaseous products, said pyrolyzer being at a temperature sufficiently above 600° C. so that substantially all of the bound nitrogen is converted to nitric oxide;

(c) indicating the level of nitric oxide in said gaseous products; and (d) utilizing said nitrogen oxide level indication to indicate the presence of said compound in said sample.

32. The method of determining the presence of a nitrogen compound in a sample of material containing organically bound nitrogen as in claim 31 comprising the steps of (a) reacting the nitric oxide produced by said conversion with ozone to produce chemiluminescence, and (b) determining the magnitude of said chemiluminescence to indicate the presence of said compound in said sample.

33. A method for detecting a nitrogen compound in a sample comprising the steps of:

(a) chromatographically separating constituents of the sample;

(b) heating said separated sample in the presence of oxygen to convert all bound nitrogen into nitric oxide; and (c) indicating the level of nitric oxide in said converted sample.

34. Apparatus for determining the nitrogen content of a sample of material containing organically bound nitrogen comprising:

(a) a chromatograph for chromatographically separating constituents of said sample;

(b) a pyrolyzer for heating said separated constituents in the presence of oxygen to convert substantially all of the bound nitrogen to nitric oxide;

(c) a chemiluminescent detector responsive to the magnitude of the nitric oxide thereby produced from said constituents to indicate the nitrogen content in said sample.

35. Apparatus as in claim 34 further including an indicator for the magnitude of said reaction.

36. Apparatus as in claim 34 wherein said pyrolyzer includes means for heating the constituents at a temperature within the range of about 600° C. to 1700° C.

* * * * *